United States Patent [19]

Keeler, Jr.

[11] Patent Number: 5,279,965

[45] Date of Patent: Jan. 18, 1994

[54] RECOMBINANT INFECTIOUS LARYNGOTRACHEITIS VIRUS

[76] Inventor: Calvin L. Keeler, Jr., 1320 Barksdale Rd., Newark, Del. 19711

[21] Appl. No.: 681,704

[22] Filed: Apr. 5, 1991

[51] Int. Cl.⁵ .................. C12N 15/86; C12N 5/10
[52] U.S. Cl. .................. 435/320.1; 435/69.1; 435/172.3; 435/240.2
[58] Field of Search ............ 435/320.1, 172.3, 240.1, 435/252.3, 235.1

[56] References Cited

U.S. PATENT DOCUMENTS 4,980,162 12/1990 Honda et al. .................. 424/89

OTHER PUBLICATIONS

Griffin et al., *Journal of General Virology*, vol. 71, pp. 841–850 (1990).

*Primary Examiner*—Richard A. Schwartz
*Assistant Examiner*—David Guzo
*Attorney, Agent, or Firm*—Donna Bobrowicz; William M. Blackstone

[57] ABSTRACT

The present invention is concerned with the preparation of an Infectious Laryngotracheitis Virus (ILTV) mutant which does not produce a functional thymidine kinase enzyme as a result of a mutation in the TK gene, and its preparation.

The invention also relates to an ILTV mutant containing a heterologous gene encoding an antigen of an avian pathogen incorporated into the TK gene. Such an ILTV mutant can be applied as a vector vaccine to induce an immune response after infection of an appropriate host animal.

7 Claims, 1 Drawing Sheet

RECOMBINANT INFECTIOUS LARYNGOTRACHEITIS VIRUS

BACKGROUND OF THE INVENTION

The present invention is concerned with an Infectious Laryngotracheitis Virus (ILTV) mutant, a recombinant vector molecule comprising ILTV DNA, a host cell transformed with said recombinant vector molecule, a process for the preparation of said ILTV mutant, a cell culture infected with the ILTV mutant, a vaccine derived from the ILTV mutant as well as a process for the preparation of such a vaccine.

Infectious laryngotracheitis (ILT) is a respiratory disease of poultry which has also been reported in pheasants and turkeys. Acute forms of the disease are characterized by signs of respiratory distress accompanied by gasping and expectoration of bloody exudate. In addition, the mucous membranes of the trachea become swollen and hemorrhagic. This epizootic form of the disease spreads rapidly and can affect up to 90-100% of an infected flock. Mortality generally averages between 10 and 20%. Milder forms of the disease are characterized by watery eyes, conjunctivitis, persistent nasal discharge and a reduction in egg production. In the absence of the acute signs of the disease laboratory confirmation must be obtained. Virus can be readily isolated from tracheal or lung tissue and the demonstration of intranuclear inclusion bodies in tracheal or conjunctival tissue is diagnostic of infectious laryngotracheitis virus. In addition, rapid identification can be made with the use of fluorescent antibodies.

The etiological agent of ILT is infectious laryngotracheitis virus (ILTV), an alpha-herpesvirus containing a linear double-stranded DNA genome approximately 150 kilobase pairs (kb) in length. ILTV has been found to exist in two isomeric forms and exhibits the physical characteristics of class 2 herpesviruses such as pseudorabies virus (PRV) and equine herpesvirus 1 (EHV-1).

Control by vaccination of ILTV infection has been a long-sought goal.

In general, attenuated live virus vaccines are preferred because they evoke a more long-lasting immune response (often both humoral and cellular) and are easy to produce.

Presently live infectious laryngotracheitis vaccines are derived from multiple passages in embryonated eggs. Vaccination has generally been used only in areas where the disease is endemic since vaccination can result in the occurence of long term "carrier" birds. Latent infections can be established in the absence of clinical signs and by low levels of virus (450 PFU).

Moreover, although at present animals can be protected against infection of ILTV with live vaccines, these vaccines suffer from a number of drawbacks. These live viral vaccines presently inoculate animals with inadequately attenuated pathogenic virus. Furthermore, because of the attenuation by serial passages uncontrolled mutations are introduced into the viral genome, resulting in a population of virus particles heterogeneous in their virulence and immunizing properties. In addition it is well known that such traditional attenuated live virus vaccines can revert to virulence resulting in disease of the inoculated animals and the possible spread of the pathogen to other animals. In addition, vaccination with existing ILTV vaccine strains seroconverts these animals to positive using ILTV-specific assays such as Elisa's. As a result, these animals can no longer be differentiated from (latent) carriers infected with more virulent field strains of ILTV.

The development of techniques for controlled manipulation of genetic material has allowed the possibility of obtaining attenuated virus vaccines which avoid the disadvantages of the classic attenuated virus vaccines.

It is an object of the present invention to provide an ILTV mutant which can be used for the preparation of a vaccine against ILTV infection, the mutant viruses being attenuated in a controlled way in a manner which excludes the reversion to virulence and which still elicits a strong immune response in host animals.

It is another object of the present invention to provide a mutant ILTV which can be used not only for the preparation of a vaccine against ILTV infection but also against other avian infectious diseases.

It is a further object of the present invention to produce subunit vaccines, pharmaceutical and diagnostic preparations comprising a heterologous polypeptide expressed by an ILTV mutant according to the invention.

SUMMARY OF THE INVENTION

Figure 1:
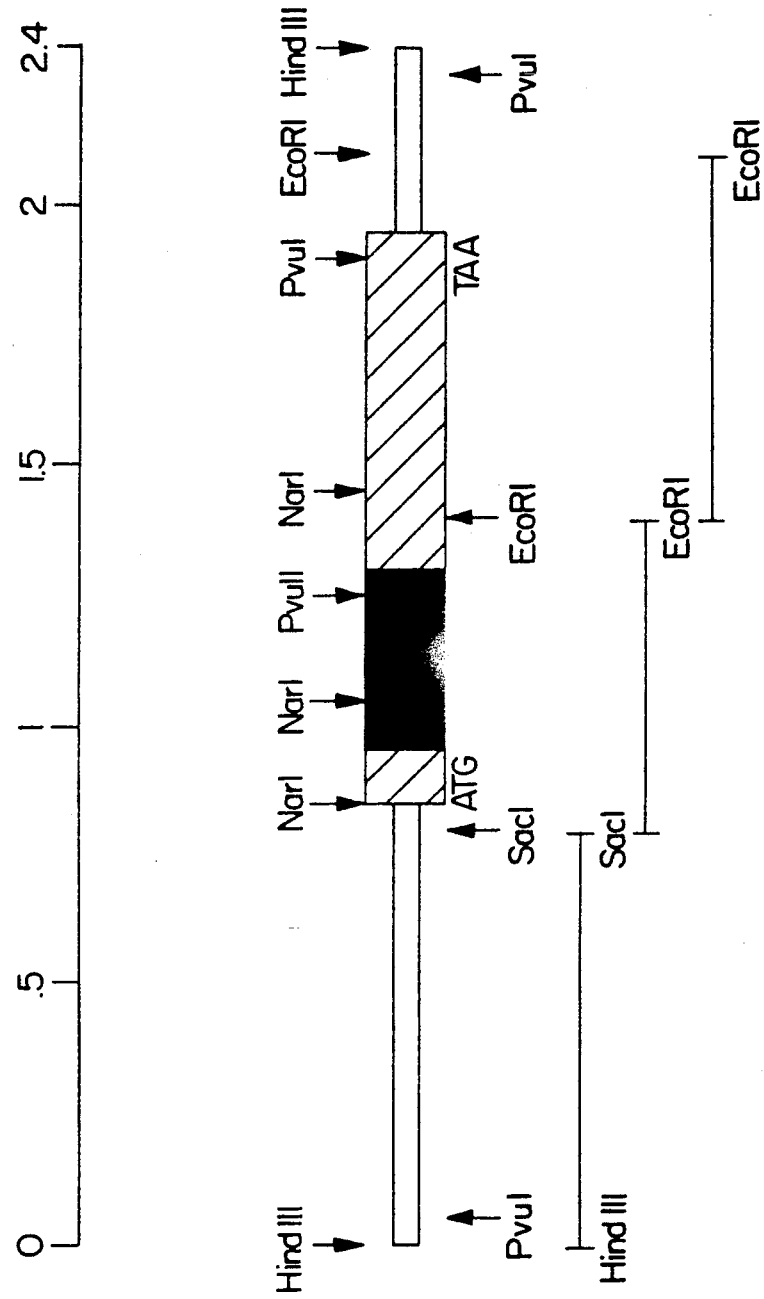
FIG. 1 is a restriction enzyme map of the 2.4 kb ILTV TK containing insert of plasmid pDE506.

The present invention is an Infectious Laryngotracheitis Virus (ILTV) mutant comprising a mutation in the gene encoding thymidine kinase, wherein the ILTV mutant lacks the ability to produce a functional thymidine kinase. The mutation may occur through the deletion of at least a fragment of the thymidine kinase gene or through the insertion of a heterologous nucleic acid sequence into the region of the thymidine kinase gene. In order to protect poultry from the ILTV and other avian pathogens, the heterologous nucleic acid sequence should be derived from another avian pathogen and should produce an antigenic polypeptide, so that when inoculated with the recombinant ILTV, the poultry will raise immunologic defenses to both the ILTV and the other avian pathogen.

The invention also comprises vaccines derived from the recombinant ILTV, recombinant vector molecules comprising the mutated thymidine kinase gene, the process for protecting poultry against infection with ILTV and at least one other avian pathogen.

DETAILED DESCRIPTION OF THE INVENTION

According to the present invention such a mutant ILTV is characterized in that it does not produce a functional thymidine kinase (TK$^-$) as a result of a mutation in the gene encoding thymidine kinase.

The term "mutation" means any change introduced into the gene encoding TK resulting in a mutated gene not capable of expressing a polypeptide with TK activity. This mutation may be an insertion, deletion and/or substitution in the TK gene.

A preferred ILTV mutant according to the invention does not produce a functional TK as a result of a deletion and/or insertion of an oligo- or polynucleotide sequence in the gene encoding TK.

Preferably, the mutation is introduced in the ILTV genomic region encoding the TK enzyme having an amino acid sequence shown in SEQ ID NO:2.

The gene encoding thymidine kinase was mapped within a 2,4 kb HindIII fragment of the ILTV genome (FIG. 1). The nucleic acid sequence of the TK gene was determined and is shown in SEQ ID NO: 1. From these data a restriction enzyme map can be deduced indicating the cleavage sites to be used for the genetic manipulation of the gene.

The TK gene consists of 1089 nucleotides encoding a 363 amino acid enzyme with a predicted molecular weight of about 40 kD (SEQ ID NO:1,2). The efficiency of the expression of TK is regulated by the presence of expression control sequences. For example promoter sequences are involved in the binding of RNA polymerase to the DNA template and control the site and onset of RNA transcription. Such sequences are often found within a 100 bp region before the transcription initiation site. Downstream transcriptional control signals are inter alia, the transcription termination codon and a polyadenylation signal. The TATA box positioned at nucleotide 47 is the putative promoter TATA box of the ILTV TK gene. A potential region for binding with eukaryotic transcription factors (CAAT-box) is located 36 bases upstream of the TATA box.

It will be understood that for the DNA sequence of the ILTV TK gene natural variations can exist between individual ILTV viruses. These variations may result in a change of one or more nucleotides in the TK gene which, however, still encodes a functional TK.

Moreover, the potential exists to use genetic engineering technology to bring about above-mentioned variations resulting in a DNA sequence related to the sequence shown in SEQ ID NO: 1 which still encodes a functional TK. It is clear that ILTV mutants comprising a mutation in such a related nucleic acid sequence are also included within the scope of the invention.

Although, the ILTV mutant according to the invention is derived from strain 632, an isolate recovered from infected tissues of 8 week old broilers by the Poultry Diagnostic Laboratory of the University of Delaware, any ILTV strain can be used to prepare the ILTV mutant, e.g. the USDA challenge strain or one of the commercial ILT vaccine strains.

ILTV deletion mutants of the present invention contain a TK gene from which a DNA fragment has been deleted so that no functional TK enzyme is produced upon infection with the virus, e.g. as result of a change of the tertiary structure of the altered TK protein or as a result of a shift of the reading frame.

In addition the deletion in the genome of the ILTV mutant may comprise the complete TK gene.

ILTV mutants according to the invention can also be obtained by inserting a nucleic acid sequence into the TK coding region thereby preventing the expression of a functional TK enzyme. Such a nucleic acid sequence can inter alia be an oligonucleotide, for example of about 10-60 bp, preferably also containing one or more translational stop codons, or a gene encoding a polypeptide. Said nucleic acid sequence can be derived from any source, e.g. synthetic, viral, prokaryotic or eukaryotic.

A suitable oligonucleotide that can be used for the incorporation into the TK gene has the formula (SEQ ID NO:3):

5'-TAGGCTAGAATTCTAGCCTA-3'
3'-ATCCGATCTTAAGATCGGAT-5'

This oligonucleotide comprises three translational stop codons, TAG, in each of the possible three reading frames, in both directions. Moreover, it contains an EcoRI recognition site, GAATTC, and further, the oligonucleotide is a palindrome. Insertion of this double-stranded oligonucleotide into any gene encoding a protein, in any orientation, in any reading frame leads to termination of the translation of the mRNA of that gene. The presence of the EcoRI recognition site in the oligonucleotide facilitates the determination of the insertion site of the oligonucleotide, as well as further manipulation of the clone in which the oligonucleotide has been inserted.

The above-mentioned oligonucleotide may be obtained in a known way by synthesis by means of the fosforamidite method.

In another embodiment of the present invention the ILTV deletion mutants can contain above-mentioned nucleic acid sequence in place of the deleted ILTV DNA.

The present invention also provides a mutant ILTV which can be used not only for the preparation of a vaccine against ILTV infection but also against other avian infectious diseases. Such a vector vaccine based on a safe live attenuated ILTV mutant offers the possibility to immunize birds against other pathogens by the expression of antigens of said pathogens within infected cells of the immunized host animal and can be obtained by inserting a heterologous nucleic acid sequence encoding a polypeptide heterologous to ILTV in an insertion-region of the ILTV genome. The term "heterologous" indicates that the nucleic acid sequence is not normally present in nature in the ILTV genome.

However, the prerequisite for a useful ILTV vector is that the heterologous nucleic acid sequence is incorporated in a permissive position or region of the genomic ILTV sequence, i.e. a position or region which can be used for the incorporation of a heterologous sequence without disrupting essential functions of ILTV such as those necessary for infection or replication. Such a region is called an insertion-region.

According to the present invention ILTV mutants are provided which can be used as a viral vector, characterized in that said mutants do not produce a functional TK as a result of an insertion in the gene encoding TK of a heterologous nucleic acid sequence encoding a polypeptide.

ILTV insertion mutants as described above having a heterologous nucleic acid sequence inserted in place of deleted TK DNA are also within the scope of the present invention.

ILTV insertion mutants are infective viruses which have been genetically modified by the incorporation into the virus genome of a heterologous nucleic acid sequence, i.e. a gene which codes for a protein or part thereof said gene being different from the genes naturally present in ILTV.

On infection of a cell by the ILTV insertion mutant, the heterologous gene is expressed in the form of a heterologous polypeptide.

The term "polypeptide" refers to a molecular chain of amino acids with a biological activity, does not refer to a specific length of the product and if required can be modified in vivo or in vitro, for example by glycosylation, amidation, carboxylation or phosphorylation. Thus peptide, oligopeptides and proteins are included within the definition of polypeptide.

The heterologous nucleic acid sequence to be incorporated into the ILTV genome according to the present invention can be derived from any source, e.g. viral, prokaryotic, eukaryotic or synthetic. Said nucleic acid sequence can be derived from a pathogen, preferably an avian pathogen, which after insertion into the ILTV genome can be applied to induce immunity against disease. Preferably, nucleic acid sequences derived from Marek's Disease virus (MDV), Newcastle Disease virus (NDV), Infectious bronchitis virus (IBV), Infectious Bursal Disease virus (IBDV), Chicken Anemia Agent (CAA), Reo virus, Avian Retro virus, Fowl Adeno virus, Turkey Rhinotracheitis virus, E. coli and Eimeria species are contemplated for incorporation into the insertion-region of the ILTV genome.

Furthermore, nucleic acid sequences encoding polypeptides for pharmaceutical or diagnostic application, in particular immune modulators such as lymphokines, interferons or cytokines, may be incorporated into said insertion-region.

An essential requirement for the expression of the heterologous nucleic acid sequence in a ILTV mutant is an adequate promoter operably linked to the heterologous nucleic acid sequence. It is obvious to those skilled in the art that the choice of a promoter extends to any eukaryotic, prokaryotic or viral promoter capable of directing gene transcription in cells infected by the ILTV mutant, such as the SV-40 promoter (Science 222, 524-527, 1983) or, e.g., the metallothionein promoter (Nature 296, 39-42, 1982) or a heat shock promoter (Voellmy et al., Proc. Natl. Acad. Sci. USA 82, 4949-53, 1985) or the human cytomegalovirus IE promoter or promoters present in ILTV, e.g. the TK promoter.

Well-known procedures for inserting DNA sequences into a cloning vector and in vivo homologous recombination can be used to introduce a deletion and/or an insertion into the ILTV genome (Maniatis, T. et al. (1989) in "Molecular cloning", second edition, Cold Spring Harbor Laboratory; European Patent Application 74.808; Roizman, B. and Jenkins, F. J. (1985), Science 229, 1208; Higuchi, R. et al. (1988), Nucleic Acids Res. 16, 7351). Briefly, this can be accomplished by constructing a recombinant vector molecule for recombination with ILTV DNA. Such a recombinant vector molecule may be derived from any suitable plasmid, cosmid, virus or phage, plasmids being most preferred, and contains ILTV DNA possibly having a heterologous nucleic acid sequence inserted therein, if desired operably linked to a promoter. Examples of suitable cloning vectors are plasmid vectors such as pBR322, the various pUC and Bluescript plasmids, bacteriophages, e.g. λ gt-WES-λ B, charon 28 and the M13mp phages or viral vectors such as SV40, Bovine papillomavirus, Polyoma and Adeno viruses. Vectors to be used in the present invention are further outlined in the art, e.g. Rodriguez, R. L. and D. T. Denhardt, edit., Vectors: A survey of molecular cloning vectors and their uses, Butterworths, 1988.

First, an ILTV DNA fragment comprising the insertion region, i.e. the TK gene, is inserted into the cloning vector using standard recDNA techniques. Said DNA fragment may comprise part of the TK gene or substantially the complete TK gene, and if desired flanking sequences thereof. It is also possible that the DNA fragment comprises TK flanking sequences from which the TK gene is deleted. Second, if an ILTV TK deletion mutant is to be obtained at least part of TK gene is deleted from the recombinant vector molecule obtained from the first step. This can be achieved for example by appropriate exonuclease III digestion or restriction enzyme treatment of the recombinant vector molecule from the first step. In the case an ILTV insertion mutant is to be obtained the nucleic acid sequence is inserted into the TK gene present in the recombinant vector molecule of the first step or in place of the TK DNA deleted from said recombinant vector molecule. The ILTV DNA sequences which flank the deleted TK DNA or the inserted nucleic acid sequence should be of appropriate length as to allow homologous recombination with the wild-type viral ILTV genome to occur.

If desired, a construct can be made which contains two or more different inserted heterologous nucleic acid sequences derived from e.g. the same or different pathogens said sequences being flanked by insertion-region sequences of ILTV defined herein. Such a recombinant DNA molecule can be employed to produce an ILTV mutant which expresses two or more different antigenic polypeptides to provide a multivalent vaccine.

Thereafter, cells, for example chicken embryo liver cells or chicken kidney cells can be transfected with ILTV DNA in the presence of the recombinant vector molecule containing the inserted heterologous nucleic acid sequence flanked by appropriate ILTV sequences whereby recombination occurs between the corresponding regions in the recombinant vector molecule and the ILTV genome. Recombination can also be brought about by transfecting ILTV genomic DNA containing host cells with DNA containing the heterologous nucleic acid sequence flanked by appropriate flanking insertion-region sequences without vector DNA sequences.

Recombinant viral progeny is thereafter produced in cell culture and can be selected for example genotypically or phenotypically, e.g. by hybridization, detecting enzyme activity encoded by a gene co-integrated along with the heterologous nucleic acid sequence, screening for ILTV mutants which do not produce functional TK (Roizman, B. and Jenkins, F. J. (1985), supra) or detecting the antigenic heterologous polypeptide expressed by the ILTV mutant immunologically. The selected ILTV mutant can be cultured on a large scale in cell culture whereafter ILTV mutant containing material or heterologous polypeptides expressed by said ILTV can be collected therefrom. Alternatively, mutant ILTV could be generated by cotransfection of several cosmids, containing a set of 30-40 kb DNA fragments which reconstitute the entire ILTV genome, and one of these cosmids containing an insertion and/or deletion into ILTV TK DNA.

A preferred ILTV mutant according to the invention contains a mutation in the TK gene created by deleting the DNA between two NarI sites, 600 base pairs, within the TK gene (FIG. 1). This results in an out-of-frame 200 amino acid deletion which abolishes enzymatic activity.

Moreover, the resulting deletion creates a preferred unique NarI site within the TK gene for the insertion of a heterologous nucleic acid sequence.

According to the present invention a live attenuated ILTV mutant which does not produce a functional TK, and if desired expresses one or more different heterologous polypeptides of specific pathogens can be used to vaccinate chickens, susceptible to ILTV and these pathogens. Vaccination with such a live vaccine is preferably followed by replication of the ILTV mutant within the inoculated host, expressing in vivo ILTV polypeptides, and if desired heterologous polypeptides.

An immune response will subsequently be elicited against ILTV and the heterologous polypeptides. An animal vaccinated with such an ILTV mutant will be immune for a certain period to subsequent infection of ILTV and above-mentioned pathogen(s).

An ILTV mutant according to the invention optionally containing and expressing one or more different heterologous polypeptides can serve as a monovalent or multivalent vaccine.

An ILTV mutant according to the invention can also be used to prepare an inactivated vaccine.

For administration to animals, the ILTV mutant according to the presentation can be given inter alia by aerosol, spray, drinking water, orally, intradermally, subcutaneously or intramuscularly. It is preferred to vaccinate the chickens by intranasal administration.

In addition to the ILTV mutant described above a vaccine according to the invention also comprises a pharmaceutically acceptable carrier compatible with the ILTV mutant. As a pharmaceutically acceptable carrier a sterilized isotonic solution such as a physiological saline and a phosphate buffer may be added to the ILTV mutant. Further suitable excipients are skimmed milk, glycerol, dextrose and the like. In addition, if desired, the vaccine can contain amounts of auxiliary substances which enhance the effectiveness of the vaccine, such as emulsifiers and adjuvants.

The vaccine according to the invention may also be in a lyophilized form.

The vaccine according to the invention is administered in such amount as will be prophylactically effective, i.e. the amount of immunizing antigen that will induce immunity in a chicken against challenge by a virulent ILTV. Immunity is defined as the induction of a significant level of protection in a population of chickens after vaccination compared to an unvaccinated group.

A dose of $10^2$ to $10^5$ EID$_{50}$ of the ILTV mutant per chicken is recommended in general.

It is also possible to produce subunit vaccines, pharmaceutical and diagnostic preparations comprising a heterologous polypeptide expressed by an ILTV mutant according to the invention. This can be achieved by culturing cells infected with said ILTV mutant under conditions that promote expression of the heterologous polypeptide. The heterologous polypeptide may then be purified with conventional techniques to a certain extent depending on its intended use and processed further into a preparation with immunizing therapeutic or diagnostic activity.

The above described active immunization against specific pathogens will be applied as a protective treatment in healthy animals. It goes without saying that animals already infected with a specific pathogen can be treated with antiserum comprising antibodies evoked by an ILTV mutant according to the invention. Antiserum directed against an ILTV mutant according to the invention can be prepared by immunizing animals with an effective amount of said ILTV mutant in order to elicit an appropriate immune response. Thereafter the animals are bled and antiserum can be prepared.

The following examples describe the isolation and characterization of the ILTV insertion region and the preparation of an ILTV mutant with a deletion and insertion in the TK gene. These examples are given merely for illustration of the present invention and are not to be construed as a limitation on the invention in any way.

EXAMPLE 1

Isolation and Characterization of ILTV Insertion Region

1. Culturing of ILTV

ILTV strain 632 is a virulent field isolate of ILTV isolated in Delaware from a flock of eight week old roasters. Virus was propagated on monolayers of primary chicken embryonic liver cells (CEL) in Dulbecco modified essential medium (DMEM) supplemented with 10% fetal bovine serum. Cells were prepared from seventeen day embryos by the warm trypsin aggregation technique (Freshney, R.I., in: Culture of Animal Cells, A Manual of Basic Techniques, Alan R. Liss, 1983).

2. Preparation of ILTV DNA

A modification of the Triton X-100 procedure of Pignatti et al. (Virology 93, 260, 1979) was used to purify ILTV DNA. Cells were infected with ILTV at a multiplicity of infection (MOI) of 1. Infected cell pellet was mixed with nine volumes of lysing solution (0.25% Triton X-100, 10 mM EDTA, 10 mM Tris-HCl, pH 7.9), and incubated at room temperature for 10 min. Once NaCl was added to a final concentration of 0.2M the mixture was centrifuged at $1000 \times g$ for 10 min. at 4° C. The supernatant was deproteinized with Proteinase K, extracted twice with phenol and viral nucleic acid was precipitated with two volumes of ethanol. The pellet was resuspended in water and contaminating cellular RNA was removed by centrifugation through a 10–40% sucrose gradient. Fractions containing viral DNA were determined by agarose gel electrophoresis, pooled, and concentrated.

3. Polymerase Chain Reaction

Polymerase chain reaction (PCR) was performed on purified genomic ILTV DNA using the thermostable DNA polymerase of Thermus aquaticus (Perkin-Elmer Cetus Instruments, Norwalk, Conn.) as described by Saiki et al. (Science 239, 487, 1985) and modified by Nunberg et al. (J. Virol. 63, 3240, 1989). Degenerate oligonucleotide primers as shown in the Table were used at a concentration of 50 or 100 pm per 50 μl reaction.

TABLE

| Primers | Thymidine kinase gene oligonucleotide primers Sequence | | | | | |
|---|---|---|---|---|---|---|
| | D | G | P/A | H/Y | G | |
| +1 5' | tcaaagctta$^a$-GAY$^b$ | GGN | SCN | YAY | GG 3' | |
| | D | R | H | P/A | | |
| −2 | 3' CTR | KCN | GTR | SG-cttaagctc 5' | | |

$^a$Actual TK sequence is in uppercase letters; restriction site extensions added to the primers are shown in lowercase letters.
$^b$The International Union of Pure and Applied Chemistry symbols used to denote multiple nucleotides are as follows: Y = C + T; R = A + G; S = C + G; K = G + T; N = A + C + G + T.

PCR cycles were as described in the references, except that the annealing temperature of the first five cycles was reduced to 37° C. to facilitate the annealing of short oligonucleotides. Subsequent cycles utilized an annealing temperature of 50° C. PCR products were analyzed and purified from 1.4% low melting temperature (LMT) agarose gels. Purified PCR products were cloned into Bluescript ™ plasmids (Stratagene, La Jolla, Calif.) after restriction endonuclease digestion of cleavage sites contained within the primer sequences.

Restriction enzymes were purchased from New England Biolabs, Inc. (Beverly, Mass.) and were used in accordance with the manufacturer's instructions. Molecular cloning techniques and southern hybridizations were as described by Ausubel et al. (edit., Current Protocols in Molecular Biology, Wiley-Interscience, 1990).

This cloned PCR fragment was subsequently used to localize and clone the entire TK gene. Viral DNA was digested with BamHI or HindIII restriction endonucleases, electrophoresed on a 0.8% agarose gel, transferred to nitrocellulose, and hybridized with $^{32}$P-labelled PCR fragment. The radiolabelled probe hybridized to 12.3 kb BamHI and 2.4 kb HindIII ILTV DNA fragments. The 2.4 kb HindIII fragment was cloned into the Bluescript TM plasmid vector pKSII creating plasmid pDE506 and was mapped with restriction enzymes using standard techniques (FIG. 1). Based on the location of the PCR product, the 2.4 kb HindIII fragment was subsequently subcloned as three smaller fragments in order to facilitate sequencing. Double stranded plasmid DNA templates were sequenced using sequencing primers appropriate to Bluescript TM plasmids as well as internal oligonucleotide primers. Both strands were sequenced with Sequenase TM II T7 DNA polymerase (U.S. Biochemicals Corp., Cleveland, Ohio) and the dideoxy chain termination method (Sanger, F. et al., Proc. Natl. Acad. Sci. USA 74, 5463, 1977). DNA and protein sequence analysis was performed using the Sequence Analysis Software Package of the University of Wisconsin Genetics Computer Group (Devereux) on the University of Delaware VMS VAX. The sequence data are presented in SEQ ID NO: 1 and 2.

EXAMPLE 2

Preparation of a ILTV Mutant Containing a TK-Deletion and Insertion

A. Construction of Plasmid Containing Mutated TK Gene

The restriction map of plasmid pDE506, containing a 2.4 kb HindIII fragment inserted in Bluescript TM II vector KS (Stratagene, La Jolla, Calif.), is presented in FIG. 1.

The 5' region of the TK-gene was deleted by digestion with NarI and recircularization of the vector molecule thereby restoring a NarI restriction site which now became unique in the plasmid derived from pDE506. The resulting plasmid was digested with NarI and blunt-ended by filling-in the extremities with a polymerase enzyme. The DNA molecule was circularized by integrating a 10-base double-stranded synthetic oligomer containing a BamHI restriction site. The resulting plasmid therefore contains a unique BamHI site at the start of the truncated TK gene. This BamHI site was used to insert a LacZ expression cassette flanked by BamHI sites. The cassette was obtained from Intervet International, Boxmeer, The Netherlands and was constructed by removing the *E. coli* β-galactosidase gene driven by the SV40 early promotor from the vector pCH110 (Pharmacia Inc., Piscataway, N.J.) and modifying the gene as follows: the 72 base pair SphI fragment near the SV40 origin of replication was replaced with a double stranded synthetic oligonucleotide having the following structure (SEQ ID NO:4):

5'- GGATCCGTCGACCATG - 3'
3'- GTACCCTAGGCAGCTG - 5'

Insertion of the linker between the two SphI restriction sites of pCH110 did not restore the recognition sequence for SphI on either site and created both a BamHI and a SalI site upstream of the SV40 early promoter. Subsequent digestion of this construct with BamHI generated a 4.0 kb expression cassette which was inserted in the BamHI site of the derivative of pDE506 containing a truncated TK-gene.

B. Transfection

The resulting plasmid containing the LacZ cassette inserted at the 5'-end of the truncated TK-gene is cotransfected with ILTV viral DNA into embryo liver cells using the calcium phosphate/DNA precipitation method according to Graham, F. and v.d. Eb, A., (Virology 52, 456, 1973) with modifications described by Morgan et al. (Avian Diseases 34, 345, 1990).

Plaques containing ILTV which has integrated the LacZ gene as a result of double reciprocal recombination between the viral genome and the plasmid DNA, are detected by staining with the substrate Bluo-gal (Gibco-BRL, Gaithersburg, Md.) using concentrations in the medium of about 0.2 mg/ml.

Blue-staining positive plaques are selected and virus is plated on fresh chicken embryonic cells in appropriate serial dilutions. This cycle is repeated untill a stable homogeneous plaque-purified isolate of recombinant ILTV is obtained.

I claim:

1. An Infectious Laryngotracheitis Virus (ILTV) mutant comprising a mutation in the gene encoding thymidine kinase, wherein the ILTV mutant lacks the ability to produce functional thymidine kinase.

2. A cell infected with an ILTV mutant according to claim 1.

3. An ILTV mutant according to claim 1, wherein the mutation is selected from the group consisting of a deletion, an insertion, and a deletion and insertion.

4. An ITLV mutant according to claim 3, wherein at least one heterologous nucleic acid molecule from an avian pathogen selected from the group consisting of a Marek's Disease Virus, Newcastle Disease Virus, Infectious Bronchitis Virus, Infectious Bursal Disease Virus, Reo Virus, Avian Retro Virus, Turkey Rhinotracheitis Virus, E. coil and Eimeria encoding a polypeptide is inserted into the thymidine kinase locus and is under the control of the endogenous ILTV thymidine kinase gene promoter.

5. A recombinant DNA vector molecule comprising a portion of the ILTV thymidine kinase gene and flanking DNA required for facilitating homologous recombination between said vector and ILTV genomic DNA.

6. A recombinant vector molecule according to claim 5, wherein the molecule contains a mutation selected from the group consisting of a deletion, an insertion and a deletion and insertion in the thymidine kinase gene.

7. A host cell comprising a chicken embryo liver cell or chicken embryo kidney cell transformed with a recombinant vector molecule according to claim 6.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1320 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Infectious laryngotracheitis virus
( C ) INDIVIDUAL ISOLATE: 632

( i x ) FEATURE:
( A ) NAME/KEY: CAATsignal ( B ) LOCATION: 8..11

( i x ) FEATURE:
    ( A ) NAME/KEY: TATAsignal
    ( B ) LOCATION: 47..50

( i x ) FEATURE:
    ( A ) NAME/KEY: CDS
    ( B ) LOCATION: 161..1249
    ( D ) OTHER INFORMATION: /label=TKgene ( x i ) SEQUENCE DESCRIPTION: SEQ ID NO:1:

```
ATGACTACAA TTTTGCCCCC GGCAGGTTTG CATTGGGGAA TTATCGTATA GGCCAGCCTT      60

CCGTCTCCAC CCCCTTCAAA GACTTCCTCC AGTGATCTGA CGAGAGCTCG GTAAAAGCGA     120

TTATGGCAAC GGATTCCGGC ATTTAGTCTA GCCCGCAGAG ATG GCC GTA GCT GGC      175
                                             Met Ala Val Ala Gly
                                              1               5

GCC GTG AAA ACT TCC GGT GGT GTG CAG TTT TGC TCC GAG TTC GAG AAC      223
Ala Val Lys Thr Ser Gly Gly Val Gln Phe Cys Ser Glu Phe Glu Asn
             10                  15                  20

GAT GAC TCC GAC TTT CGC CGC GTT GTA CTT CTT TAC GTC GAC GGG CCA      271
Asp Asp Ser Asp Phe Arg Arg Val Val Leu Leu Tyr Val Asp Gly Pro
                 25                  30                  35

TTC GGA GTC GGT AAA ACA GTC ACT GCA AAG ACG TTG ATG CAA ATG CCA      319
Phe Gly Val Gly Lys Thr Val Thr Ala Lys Thr Leu Met Gln Met Pro
         40                  45                  50

AAT TGG AGA GGT TGC CGT CTA TAC TTA GCG GAA CCT ATG CAA GCA TGG      367
Asn Trp Arg Gly Cys Arg Leu Tyr Leu Ala Glu Pro Met Gln Ala Trp
 55                  60                  65

CGC CAA TGG TTT GGC GGA GCG GAT ATG ATC AAA GAA ATT AAT GAA ATA      415
Arg Gln Trp Phe Gly Gly Ala Asp Met Ile Lys Glu Ile Asn Glu Ile
 70                  75                  80                  85

CAA ACC CTA AAG GCT TCC GGA AAA CTT GAA TGT CGG GAG GCG TCT CGT      463
Gln Thr Leu Lys Ala Ser Gly Lys Leu Glu Cys Arg Glu Ala Ser Arg
                 90                  95                 100

CGC GTA GCG GAA GTT CAG ATG ACT ATT GCT GCC CCA CTA AGA ATA ATG      511
Arg Val Ala Glu Val Gln Met Thr Ile Ala Ala Pro Leu Arg Ile Met
            105                 110                 115

AAC CAC GTC ATT TAT AAT TAT TTG GGA TCT GAA CGC TGC TAC AGC GCA      559
Asn His Val Ile Tyr Asn Tyr Leu Gly Ser Glu Arg Cys Tyr Ser Ala
        120                 125                 130

GCT GCA TCC GGA CCA GAT GAT GTC TTA TTC CTC GTA GAT AGG CAC CCA      607
Ala Ala Ser Gly Pro Asp Asp Val Leu Phe Leu Val Asp Arg His Pro
135                 140                 145

CTC GCG GCA TGT TTG TGT TTC CCT GTT GCA CAA TAT CTA AGC GGA GCG      655
Leu Ala Ala Cys Leu Cys Phe Pro Val Ala Gln Tyr Leu Ser Gly Ala
150                 155                 160                 165

CTC GAA TTT GGA GAT TTA ATA ACT TTA TTG TCA GGA ATT CCT GAC ATT      703
Leu Glu Phe Gly Asp Leu Ile Thr Leu Leu Ser Gly Ile Pro Asp Ile
                170                 175                 180

CCA ACA CAC TCC AAC ATT GTT TTA ATG GAT TTG GAT ATT TGC GAA CAG      751
Pro Thr His Ser Asn Ile Val Leu Met Asp Leu Asp Ile Cys Glu Gln
            185                 190                 195

GCA CGG CGT ATA ATA CAA AGG GGG CGC CCA GGG GAA ACG GTC GAC TGG      799
Ala Arg Arg Ile Ile Gln Arg Gly Arg Pro Gly Glu Thr Val Asp Trp
        200                 205                 210

ACG TAT TTG TGT GCA TTA CGT AAC TCG TAC ATC TGC CTC ATG AAT ACT      847
Thr Tyr Leu Cys Ala Leu Arg Asn Ser Tyr Ile Cys Leu Met Asn Thr
    215                 220                 225

ACC ACC TAC CTC CAA CGT ACA TCT TAT CCA GCA TTG TTG AAG GAG CAA      895
Thr Thr Tyr Leu Gln Arg Thr Ser Tyr Pro Ala Leu Leu Lys Glu Gln
230                 235                 240                 245
```

-continued

```
GAA GCC TTA ACA AGT GCC ACG CTC TTA AAA TTC AAG AGA GAG TGC TTA        943
Glu Ala Leu Thr Ser Ala Thr Leu Leu Lys Phe Lys Arg Glu Cys Leu
            250                 255                 260

GAA ACT GCT ACT GTT CCA GAA ATC AAT CCT TCA ATC GAC CAG ACG CTA        991
Glu Thr Ala Thr Val Pro Glu Ile Asn Pro Ser Ile Asp Gln Thr Leu
            265                 270                 275

TTT GCA ATA TTA GCT TTT GAT CAG CAA AAT GTT CAC GGG GAA AGA TTA       1039
Phe Ala Ile Leu Ala Phe Asp Gln Gln Asn Val His Gly Glu Arg Leu
            280                 285                 290

AAA ACT GTA CTT TCA TTT GTG GTT CAA AAA CTC GCG ACG GTA TTG AAA       1087
Lys Thr Val Leu Ser Phe Val Val Gln Lys Leu Ala Thr Val Leu Lys
            295                 300                 305

AAC TTG TGC ATT TTT TAC TTA CCA GCA CAT GGC CTC ACC CCG GAG GCA       1135
Asn Leu Cys Ile Phe Tyr Leu Pro Ala His Gly Leu Thr Pro Glu Ala
310             315                 320                 325

TGT GCA CTG AAA TGT TTA GAG TTT GCC GAG ACG GCA AGT TCT CTT ACA       1183
Cys Ala Leu Lys Cys Leu Glu Phe Ala Glu Thr Ala Ser Ser Leu Thr
            330                 335                 340

ACC AAA CGA GCG GCG ATC GCG AGC TTA ATT GAC GCA GTA GAG CGC TAC       1231
Thr Lys Arg Ala Ala Ile Ala Ser Leu Ile Asp Ala Val Glu Arg Tyr
            345                 350                 355

AAT GCT GAT ATG GGT TCG TAATGTTCCG CATCCATAAT CCTTCACAAT              1279
Asn Ala Asp Met Gly Ser
            360

AAGAGTATGT CCTTTACTCA TTTCCTTGCT TTGTACTCAT T                         1320
```

( 2 ) INFORMATION FOR SEQ ID NO:2:

( i ) SEQUENCE CHARACTERISTICS:
        ( A ) LENGTH: 363 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Val Ala Gly Ala Val Lys Thr Ser Gly Gly Val Gln Phe Cys
1               5                   10                  15

Ser Glu Phe Glu Asn Asp Asp Ser Asp Phe Arg Arg Val Val Leu Leu
            20                  25                  30

Tyr Val Asp Gly Pro Phe Gly Val Gly Lys Thr Val Thr Ala Lys Thr
            35                  40                  45

Leu Met Gln Met Pro Asn Trp Arg Gly Cys Arg Leu Tyr Leu Ala Glu
    50                  55                  60

Pro Met Gln Ala Trp Arg Gln Trp Phe Gly Gly Ala Asp Met Ile Lys
65                  70                  75                  80

Glu Ile Asn Glu Ile Gln Thr Leu Lys Ala Ser Gly Lys Leu Glu Cys
                85                  90                  95

Arg Glu Ala Ser Arg Arg Val Ala Glu Val Gln Met Thr Ile Ala Ala
            100                 105                 110

Pro Leu Arg Ile Met Asn His Val Ile Tyr Asn Tyr Leu Gly Ser Glu
            115                 120                 125

Arg Cys Tyr Ser Ala Ala Ala Ser Gly Pro Asp Asp Val Leu Phe Leu
            130                 135                 140

Val Asp Arg His Pro Leu Ala Ala Cys Leu Cys Phe Pro Val Ala Gln
145                 150                 155                 160

Tyr Leu Ser Gly Ala Leu Glu Phe Gly Asp Leu Ile Thr Leu Leu Ser
                165                 170                 175

Gly Ile Pro Asp Ile Pro Thr His Ser Asn Ile Val Leu Met Asp Leu
            180                 185                 190
```

-continued

| Asp | Ile | Cys 195 | Glu | Gln | Ala | Arg | Arg 200 | Ile | Ile | Gln | Arg | Gly 205 | Arg | Pro | Gly |
| --- | --- | --- | --- | --- | --- | --- | --- | --- | --- | --- | --- | --- | --- | --- | --- |
| Glu | Thr 210 | Val | Asp | Trp | Thr | Tyr 215 | Leu | Cys | Ala | Leu | Arg 220 | Asn | Ser | Tyr | Ile |
| Cys 225 | Leu | Met | Asn | Thr | Thr 230 | Thr | Tyr | Leu | Gln | Arg 235 | Thr | Ser | Tyr | Pro | Ala 240 |
| Leu | Leu | Lys | Glu | Gln 245 | Glu | Ala | Leu | Thr | Ser 250 | Ala | Thr | Leu | Leu | Lys 255 | Phe |
| Lys | Arg | Glu | Cys 260 | Leu | Glu | Thr | Ala | Thr 265 | Val | Pro | Glu | Ile | Asn 270 | Pro | Ser |
| Ile | Asp | Gln 275 | Thr | Leu | Phe | Ala | Ile 280 | Leu | Ala | Phe | Asp | Gln 285 | Gln | Asn | Val |
| His | Gly 290 | Glu | Arg | Leu | Lys | Thr 295 | Val | Leu | Ser | Phe | Val 300 | Val | Gln | Lys | Leu |
| Ala 305 | Thr | Val | Leu | Lys | Asn 310 | Leu | Cys | Ile | Phe | Tyr 315 | Leu | Pro | Ala | His | Gly 320 |
| Leu | Thr | Pro | Glu | Ala 325 | Cys | Ala | Leu | Lys | Cys 330 | Leu | Glu | Phe | Ala | Glu 335 | Thr |
| Ala | Ser | Ser | Leu 340 | Thr | Thr | Lys | Arg | Ala 345 | Ala | Ile | Ala | Ser | Leu 350 | Ile | Asp |
| Ala | Val | Glu 355 | Arg | Tyr | Asn | Ala | Asp 360 | Met | Gly | Ser | | | | | |

( 2 ) INFORMATION FOR SEQ ID NO:3:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:3:

TAGGCTAGAA TTCTAGCCTA                    20

( 2 ) INFORMATION FOR SEQ ID NO:4:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:4:

CATGGGATCC GTCGACCATG                    20